United States Patent [19]
Weaver et al.

[11] Patent Number: 5,843,028
[45] Date of Patent: *Dec. 1, 1998

[54] MULTI-LUMEN ENDOSCOPIC CATHETER

[75] Inventors: George W. Weaver, East Earl, Pa.; Harold Jacob, Lawrence, N.Y.; David F. Leighton, West Lawn; Damond C. Holsinger, New Holland, both of Pa.

[73] Assignee: Medical Innovations Corporation, Draper, Utah

[*] Notice: The term of this patent shall not extend beyond the expiration date of Pat. No. 5,599,299.

[21] Appl. No.: 706,311

[22] Filed: Aug. 30, 1996

Related U.S. Application Data

[63] Continuation of Ser. No. 189,317, Jan. 31, 1994, Pat. No. 5,599,299, which is a continuation-in-part of Ser. No. 60,434, May 11, 1993, Pat. No. 5,397,302, which is a continuation-in-part of Ser. No. 880,842, May 11, 1992, abandoned.

[51] Int. Cl.$^6$ .................................................. A61N 31/00
[52] U.S. Cl. .............................. 604/54; 604/96; 604/280
[58] Field of Search .................................. 604/49, 52–53, 604/54, 96, 102, 280; 606/108, 167, 45, 46

[56] References Cited

U.S. PATENT DOCUMENTS

| | | |
|---|---|---|
| 4,781,677 | 11/1988 | Wilcox . |
| 4,794,928 | 1/1989 | Kletschka ............................ 604/22 X |
| 4,832,023 | 5/1989 | Murphy-Chutorian et al. . |
| 4,905,667 | 3/1990 | Foerster et al. ............................ 128/4 |
| 4,927,412 | 5/1990 | Menasche . |
| 5,024,617 | 6/1991 | Karpiel . |
| 5,035,696 | 7/1991 | Rydell . |
| 5,059,177 | 10/1991 | Towne et al. . |
| 5,152,772 | 10/1992 | Sewell, Jr. . |
| 5,167,623 | 12/1992 | Cianci et al. . |
| 5,195,962 | 3/1993 | Martin et al. . |
| 5,201,732 | 4/1993 | Parins et al. . |
| 5,261,889 | 11/1993 | Laine et al. . |
| 5,273,527 | 12/1993 | Schatz et al. . |
| 5,306,237 | 4/1994 | Clement et al. . |
| 5,334,143 | 8/1994 | Carroll . |
| 5,336,227 | 8/1994 | Nakao et al. . |
| 5,342,295 | 8/1994 | Imran . |
| 5,378,230 | 1/1995 | Mahurkar . |
| 5,451,206 | 9/1995 | Young . |
| 5,486,159 | 1/1996 | Mahurkar . |
| 5,536,234 | 7/1996 | Newman . |
| 5,540,798 | 7/1996 | Demaio et al. . |
| 5,547,469 | 8/1996 | Rowland et al. . |

*Primary Examiner*—Corrine M. McDermott
*Attorney, Agent, or Firm*—Thorpe, North & Western, LLP

[57] ABSTRACT

Multi-lumen catheters are intended for advancement through the accessory channel on endoscope into a body passage into the gastrointestinal system. The catheters have two or more independent lumens extending continuously to ports at the distal tip for injection of a contrast medium simultaneously with a guide wire for ERCP procedures and for passage of accessories such as visualization devices, polypectomy snares, cytology brushes, papillotomes and stone baskets for catheterization, diagnosis and treatment within the biliary tract. Use of balloons for maintaining a catheter in fixed position in the biliary tract and for dilatation is also disclosed. The catheters employed are extrusions of a resin comprised of nylon and PEBA. The catheters may also be extruded from polyurethane. Multi-lumen catheters having a reduced diameter distal tip portion on which a dilatation balloon is located are also disclosed. The reduced diameter distal tip portion may serve as a platform for support of a stent.

17 Claims, 12 Drawing Sheets

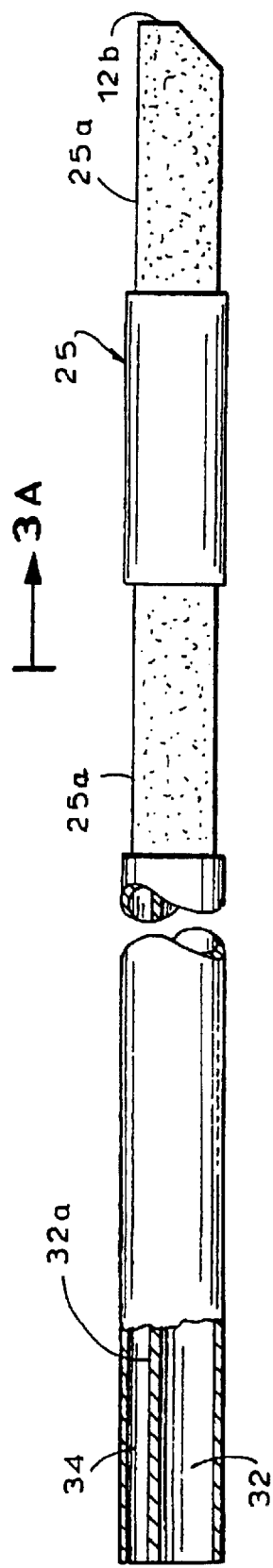
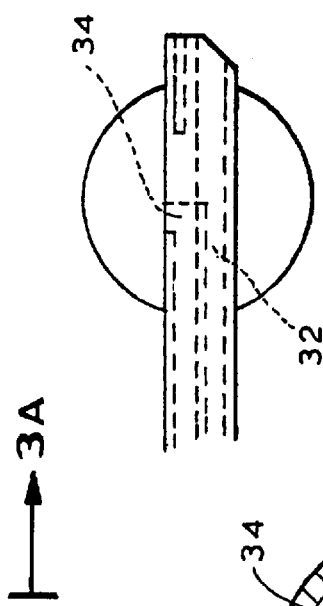
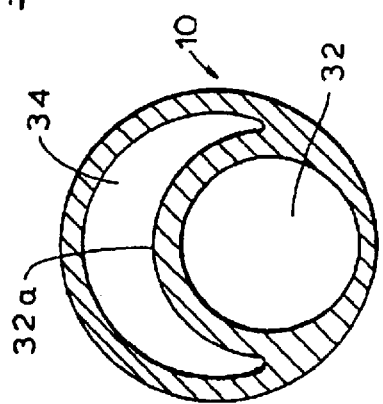
FIG. 3
FIG. 3A
FIG. 3B

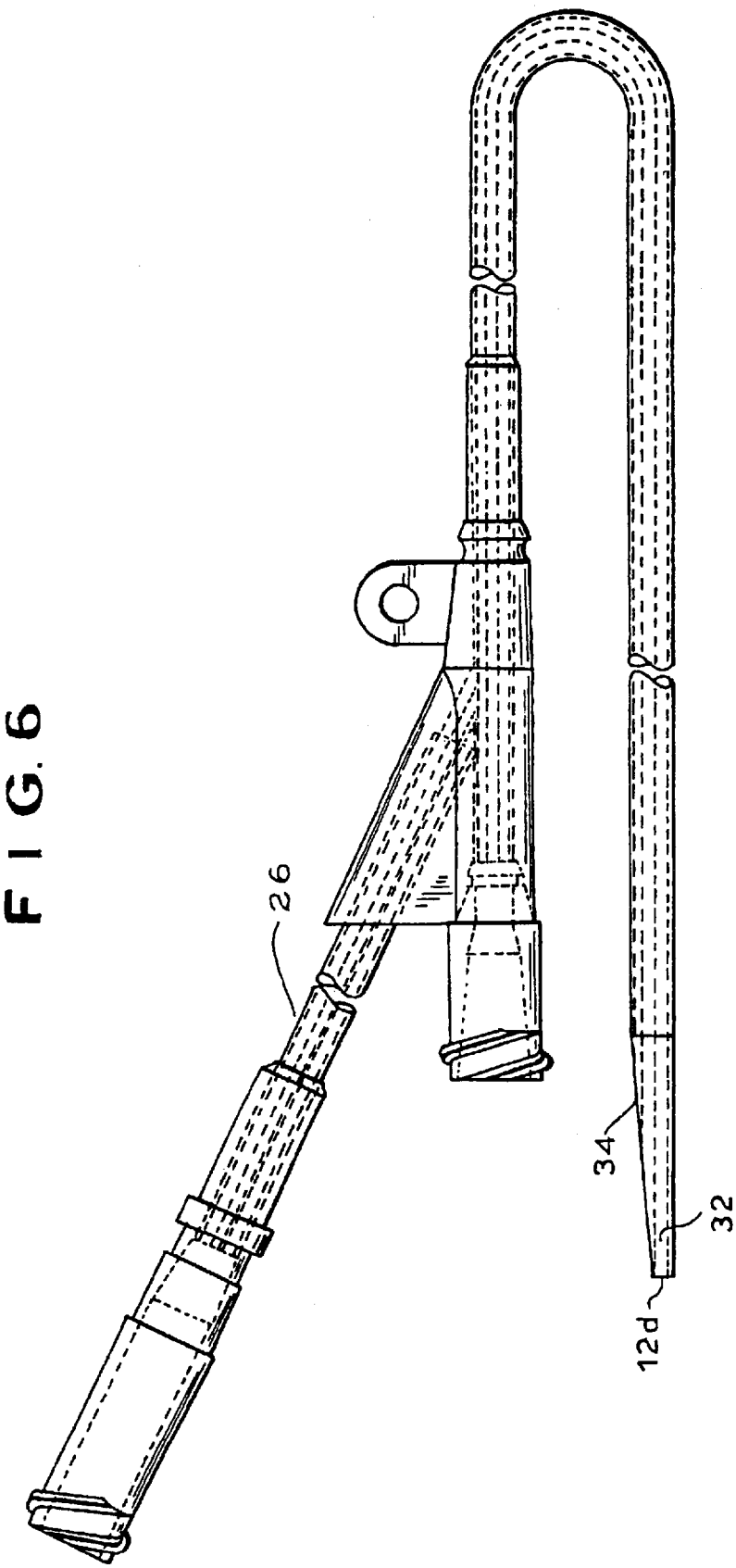

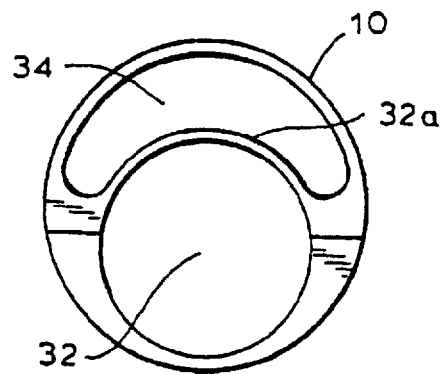
FIG. 10
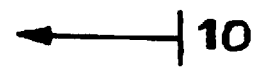
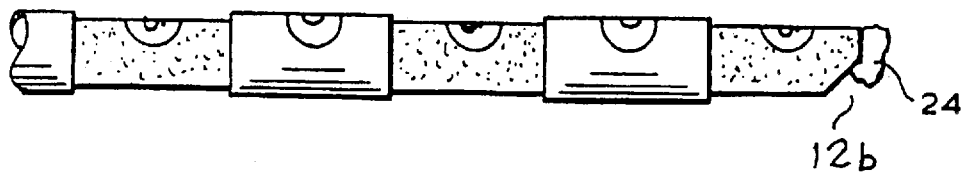
FIG. 9A
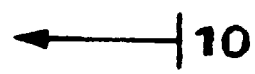
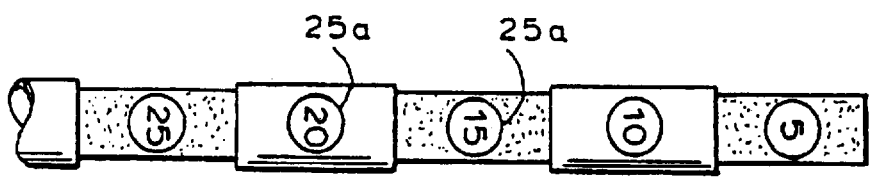
FIG. 9B

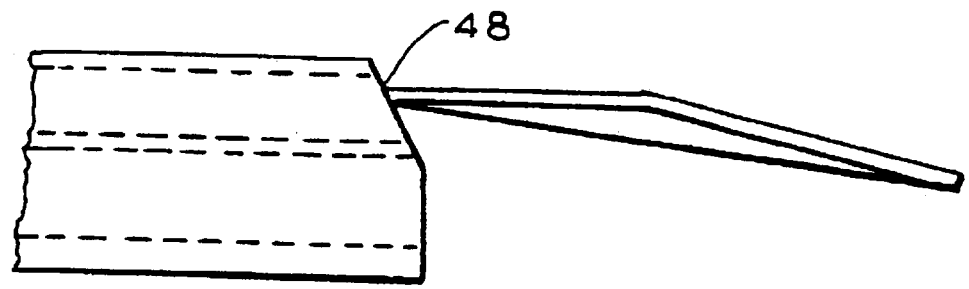
FIG. 11
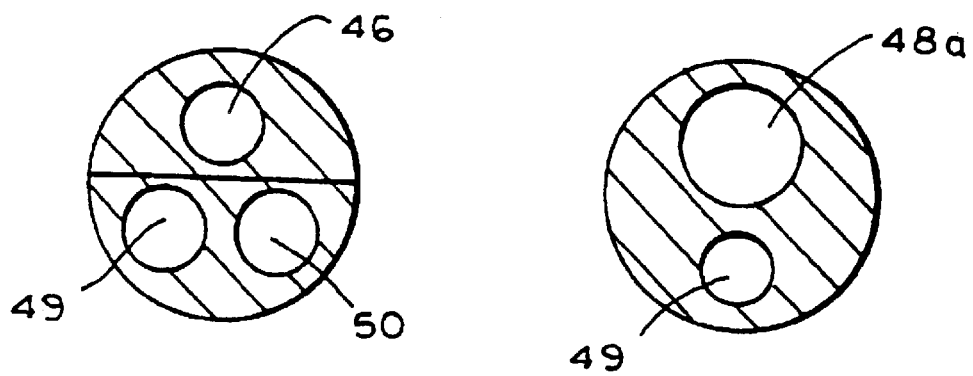
FIG. 12   FIG. 12A
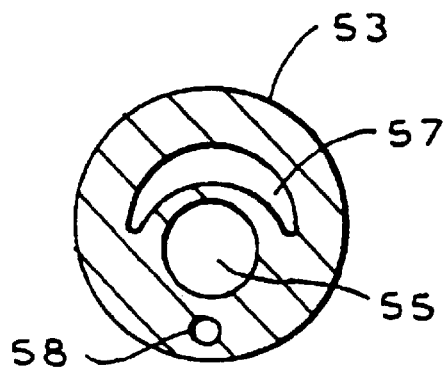 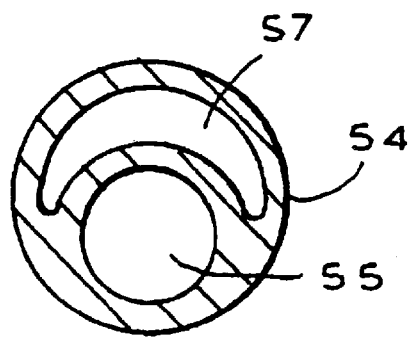
FIG. 15   FIG. 16

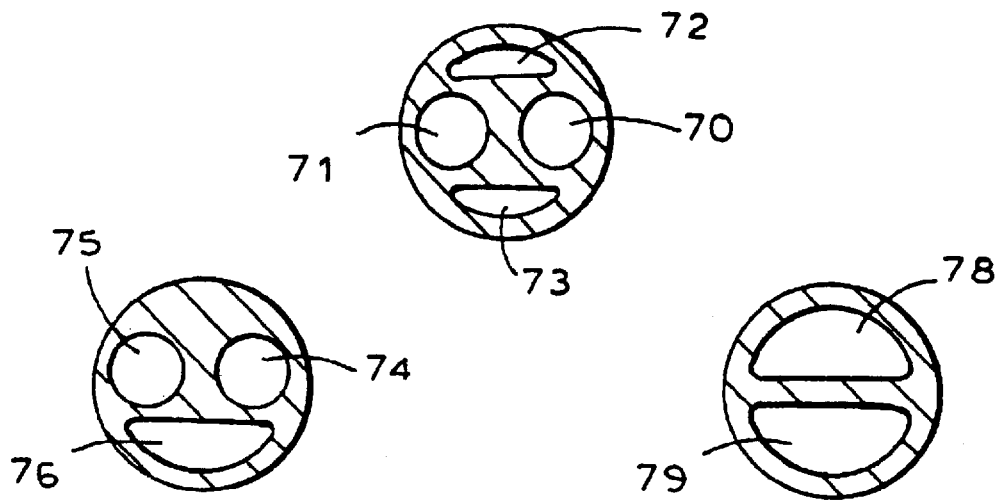
FIG. 19
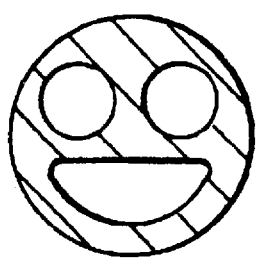
FIG. 20
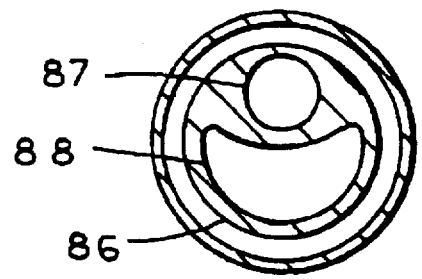
FIG. 21
FIG. 22
FIG. 23
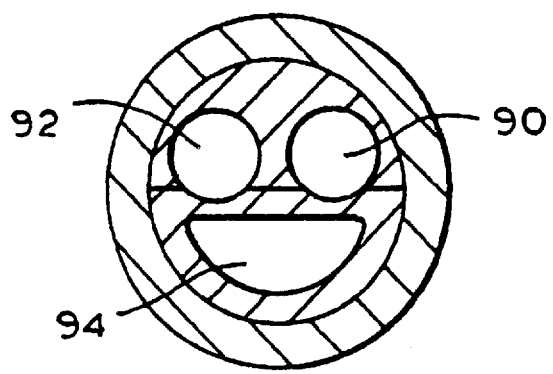
FIG. 24

MULTI-LUMEN ENDOSCOPIC CATHETER

This application is a continuation of U.S. Ser. No. 08/189,317, filed Jan. 31, 1994, now U.S. Pat. No. 5,599,299 which is a continuation-in-part of U.S. Ser. No. 08/060,434, filed May 11, 1993, now U.S. Pat. No. 5,397,302, which is a continuation-in-part of U.S. Ser. No. 07/880,842, filed May 11, 1992, now abandoned.

FIELD OF THE INVENTION

The present invention is directed to catheters adapted for passage through the accessory channel of an endoscope into a duct or passageway within the gastrointestinal system of the body. Although not limited in its applicability and scope, the invention has particular applicability to procedures which involve the advancement of the catheter to positions within the biliary tract and especially to the practice of Endoscopic Retrograde Cholangiopancreatography.

BACKGROUND OF THE INVENTION

A number of procedures have evolved in recent years using instruments intended to be inserted through an endoscope in various positions within the gastrointestinal system for the purpose of diagnosis and for therapeutic procedures, including the insertion of stents, devices for the extraction of stones from the biliary duct, the removal of polyps and the extraction of tissue for biopsy purposes.

One diagnostic technique which has come into use is Endoscopic Retrograde Cholangiopancreatography (ERCP) which is described in copending application Ser. No. 07/880,842, filed May 11, 1992. The ERCP technique is an endoscopic technique which involves the placement of a side-viewing instrument within the descending duodenum. The procedure eliminates the need for invasive surgical procedures for identifying biliary stones and other obstructions of the biliary and pancreatic ducts. As background of the invention, the ERCP technique exemplified the problems and difficulties which the present invention addresses.

Utilizing this technique, the Papilla of Vater and common biliary duct are cannulated, contrast medium injected and pancreatic ducts and the hepatobiliary tree visualized radiographically or examined with a duodeno fiberscope. Skilled medical practitioners can visualize approximately 90–95% of the biliary and pancreatic ducts using this technique.

ERCP is typically performed on an X-ray table. During the procedure, the patient's oropharynx is anesthetized with topical lidocaine, and the patient is sedated intravenously with diazepam. Atropine and glucagon are given intravenously to relax the duodenal muscles.

The ERCP procedure has heretofore typically been performed by the endoscopic introduction of a single lumen catheter into the pancreatic and common biliary ducts of a patient. Such ERCP catheters have typically been constructed from Teflon®. At times, a spring wire guide may be placed in the lumen of the catheter to assist in cannulation of the ducts. A stylet, used to stiffen the catheter, must first be removed prior to spring wire guide insertion. The introduction of the spring wire guide eliminates the ability to inject contrast medium or makes it highly cumbersome.

To summarize the procedure, an ERCP catheter is initially inserted through the endoscope and into the biliary or pancreatic ducts. If difficulty is encountered or if the operator so desires, a spring wire guide is threaded into the catheter to assist in the cannulation. After the catheter is inserted into the duct and threaded over the spring wire guide, the spring wire guide is removed. A radio-opaque contrast medium is then injected through the single lumen of the catheter in order to identify obstructions such as bile stones. Once located and identified, such stones can then be eliminated or destroyed by methods such as mechanical lithotripsy utilizing a device such as an Olympus BML-10/20 Mechanical Lithotriptor.

This method of performing ERCP has several disadvantages. Most notably, it relies upon the use of a single lumen catheter which is threaded over the spring wire guide or pushed by a stylet and then, upon the removal of the stylet or spring wire guide is then used for infusing radio-opaque contrast medium or dye into the biliary and pancreatic ducts. Unfortunately, the process of withdrawing the stylet or spring wire guide in order to clear the single lumen for contrast medium or dye infusion frequently repositions the catheter. Thus, when the radio-opaque or contrast medium is injected into the catheter, the catheter is often improperly positioned for proper fluoroscopy or X-ray visualization. Moreover, this method presents the further problem of having to repeatedly remove the stylet or an approximately six foot long spring wire guide, maintain its cleanliness and then reinsert it into the catheter. In addition, the dye is sticky and reintroduction of the guide wire is made difficult due to the frictional resistance offered by it. Finally, single lumen catheters frequently experience the problem of back-flow in which the radio-opaque dye is squirted back out the side port of the catheter and onto the administering medical professional.

The above problems often result in the need to repeat the procedure and a time consuming exercise of trial and error. Multiple attempts at properly positioning the catheter and spring wire guide are often necessary. Increased amounts of tracer dye associated with multiple injections increase the risk of pancreatitis. Because the ERCP procedure is performed under sedation, the additional time required for proper catheter positioning tends to increase the risk to the patient. Furthermore, because of the considerable expense of maintaining a procedure room, the use of single lumen ERCP catheters can add considerably to the expense of the procedure. Accordingly, practice of ERCP procedures has heretofore been limited to only the most skilled endoscopists.

SUMMARY AND OBJECTS OF THE INVENTION

The invention has particular applicability in the performing of ERCP procedures, other diagnostic and surgical procedures performed within the biliary system, as well as other parts of the gastrointestinal system in general, by the use in such procedures of catheters having at least two lumens, and preferably three or four lumens. The multi-lumen catheter assemblies of the invention are specially designed to be inserted into a duct or body passage through the accessory channel of an endoscopic instrument. A catheter assembly for use in carrying out the invention comprises, in its broadest aspects, a catheter body of substantially cylindrical shape and substantially uniform diameter having a plurality of independent lumens extending lengthwise thereof. At least two lumens exit at the distal tip of the catheter body with each exit port facing generally distally along the passage being explored axially and forwardly. The catheters of the present invention are sized to be passed through the accessory port of a conventional endoscopic instrument. The catheters have a combined length sufficient to extend the length of the standard accessory channel and into the more remote portions of the duct or passage and further have a proximal section extending proximally of the endoscope channel for a sufficient distance to allow for manipulation of the catheter by the user into the most extreme position. In the exemplary case of the biliary system, the invention allows for substantially complete exploration and visualization without the need to remove the spring wire guide. Follow-up procedures, such as stent placement, tissue sampling, use of a papillotome/ sphincterotome or the like are accomplished through a lumen of the catheter already placed and may be accompanied by periodic dye injection and visualization without removal of the catheter. For certain of these procedures, the wire guide is preferably left in place, as will be noted in the explanation which follows. A further advantageous embodiment of the invention involves a multi-lumen catheter with a reduced diameter distal tip portion on which a dilatation balloon is secured. In a related embodiment, a reduced diameter distal end portion serves as a platform for a stent.

The use of multi-lumen catheters for procedures such as described above offers many advantages over the prior art practice of using single-lumen catheters. As noted above, one important advantage is the facility for injection of contrast medium so as to attain complete visualization of a system of passages, such as the biliary tract, without the need to remove the spring wire guide. When one recognizes that a catheter for use in ERCP procedures must be approximately 200 cm in length and the spring wire guide must be an additional 200cm or so in length, the very act of removal of the spring wire guide to allow for injection of contrast medium through a single-lumen catheter can be seen to be both awkward and time consuming. Since the spring wire guide is needed again for repositioning the catheter, its extreme length and resilient nature makes it very difficult to avoid loss of sterility when it is temporarily removed from the catheter. Furthermore, when the spring wire guide is reinserted after injection of the contrast medium through the single lumen, it has been found that because the contrast medium tends to be sticky, the resistance offered within the lumen impedes reintroduction. This condition is aggravated due to the relatively small diameter and the length of the lumen through which the spring wire guide must be passed. Since the catheters can be properly placed much more easily with less trial and error, the provision of separate lumens for dye injection and guide wire placement has been found to dramatically reduce the use of tracer dye. In addition, the provision of a separate lumen for guide wire placement eliminates the risk that air will enter the biliary tract as may occur when a single lumen is used for dye and guide wire. Still further, it is highly desirable to have further lumens within the catheter to allow for other procedures, such as the introduction and removal of stents, the use of instruments, such as papillotomes, biopsy cutters, stone extractors, forceps, knives and the like. Accordingly, it is an important objective of the invention to provide a multi-lumen catheter of small enough diameter to pass through the accessory channel of the endoscopic instrument having the following characteristics: to provide for additional lumens sized to permit the aforementioned procedures within the limited cross-section available; to retain the requisite flexibility so as to facilitate passage to a final position within an extended tortuous passageway; and to maintain the patency of the lumens without bunching up or kinking as the catheter is advanced over the spring wire guide and into a final position.

One aspect of the invention is the provision of a catheter constructed from a blend of resins producing a catheter body having peak stress of at least 8000 psi and a torqueability of at least 0.3 inch ounce at body temperature, wherein torqueability is measured as resistance to twisting through 360° with one end of the catheter fixed. An important feature of the present invention involves the treatment of at least the distal end section of the catheter with a hydrophilic coating. The hydrophilic coating of the present invention provides a highly lubricated surface which is activated by the presence of moisture. In the case of a biliary catheter, the biliary fluids activate the coating as it enters the biliary passage of the patient. The hydrophilic coating serves the further function of softening the catheter body so as to increase its suppleness and kink resistance and lubricity. Further, the softened distal portion is less traumatic to the tissue within the body passage. In a preferred embodiment, the lubricous hydrophilic coating is confined to that portion of the catheter liable to be inserted within the endoscope and the body passage. This facilitates initial passage of the catheter to the desired position within the passageway, since the catheter remains in a firmer state until it contacts the body fluid. Since the coating is quite slippery, its absence from the proximal end of the catheter allows the medical professional to retain a firm grip on the catheter as it is manipulated to the desired position. The lubricous hydrophilic coating may optionally also be applied within the spring wire guide lumen and other lumens provided for the insertion of instruments.

Preferably, catheters formed according to the invention are extruded, utilizing a blend of polymers comprised of nylon, especially nylon 11, and an ester linked polyether-polyamide copolymer (PEBA). In the case of biliary catheters, catheters having two or more lumens, one of which is of sufficient diameter to allow passage of a guide wire and to allow passage of another device and the other for a dye or other injectable fluid and having an external diameter of between about 1.8 mm and about 3.8 mm can be formed by an extrusion process. These catheters, when coated with the lubricous hydrophilic coatings of the type herein referred, are extremely supple and offer a kink resistance not obtainable with prior art catheters formed of Teflon®. When formed from the resin blends of the present invention, the catheter material does not exhibit the tendency to bunch up on the wire guide as the catheter is pushed through the passageway. The catheters have good "torqueability", that is to say, the tip follows the proximal end without undue twisting when the medical professional rotates the catheter during placement.

Preferably, the catheter has a central section substantially equivalent in length to the length of the accessory channel of a standard video duodenoscope, a distal section substantially equal in length to the portion of the body passage to be negotiated and a proximal section of a length sufficient to allow for manual manipulation when the distal section is in an extreme position within the body passage. At least the distal section but not the proximal section is coated with a hydrophilic coating which provides lubricity within the passage.

By providing exit ports in the distal tip of the catheter and orienting the ports in a generally axial direction, so that devices or injectable fluids exit distally of the catheter, procedures which involve the advancement of the catheter over the spring wire guide, use of a papillotome or other instrument and injection of contrast medium at successive locations along a relatively confined duct or passageway, such as the biliary duct, are facilitated. By use of at least two lumens having ports facing generally forwardly in the direction of movement of the catheter, removal of the wire guide from the catheter during other procedures can be avoided. Direct visualization devices and other instruments can be passed through one lumen while the spring wire guide remains in place in a second lumen for ongoing repositioning of the catheter as is desired by the user. Catheters according to the invention may be provided with a dilatation balloon or a supporting surface on the distal tip portion for support of a stent. Desirably, additional lumens are reserved for the injection of a tracer dye and aspiration of biliary fluid.

BRIEF DESCRIPTION OF THE DRAWINGS

FIG. 3 is a side view, partly in section, of a dual-lumen biliary catheter body formed according to the present invention illustrating the distal tip illustrating the contrast stripes at the distal end of the catheter;

FIG. 3A is a section view illustrating the dual lumens of the biliary catheter of FIGS. 1–3 taken along line 3A—3A of FIG. 3;

FIG. 3B is a fragmentary side view of a dual-lumen catheter having a balloon at the distal tip and having the cross-sectional figuration of FIG. 3A;

FIG. 6 is a side elevational view of an alternative distal tip configuration for the biliary catheter of the present invention;

FIGS. 9A and 9B are side and top views, respectively, of a catheter of the invention having a beveled tip and digitized markings;

FIG. 10 is an end view of the catheter of FIGS. 9A and 9B;

FIGS. 11 and 12 are side and end views of the distal tip section of a triple-lumen polypectomy catheter formed according to the invention;

FIG. 12A is a cross-sectional view of a modified form of the polypectomy catheter illustrated in FIGS. 11 and 12;

FIG. 15 is a sectional view on an enlarged scale taken on line 15—15 of FIG. 13A;

FIG. 16 is a sectional view on an enlarged scale taken on line 16—16 of FIG. 13A;

FIG. 19 is a cross-sectional view of a four-lumen catheter used for the purposes of cannulating the common bile duct and the pancreatic duct;

FIG. 20 is a cross-sectional view of a triple-lumen catheter in which a papillotome is accommodated for the purpose of tissue cutting as an aid to catheter insertion;

FIG. 21 illustrates a modified form of dual-lumen catheter useful for stone removal;

FIG. 22 is a cross-sectional view of a triple-lumen catheter used for stone visualization and removal;

FIG. 23 is a cross-sectional view of an alternative embodiment of a catheter used for the purposes explained with respect to FIGS. 13A–16; and FIG. 24 is a cross-sectional view of a catheter used for stent placement and removal.

DETAILED DESCRIPTION OF THE PREFERRED EMBODIMENT

Preferred embodiments of the improved catheters of the present invention are described with reference to FIGS. 1–18, wherein unless otherwise indicated, the same numbers are utilized to denote the same or equivalent parts. For the purpose of description, the present invention will be described in the context of its use in the cannulation and visualizing of the common biliary duct of a patient pursuant to an ERCP procedure. It is to be recognized that the present invention is applicable to all ERCP procedures involving the cannulation and radiological visualization of the common biliary, pancreatic, common hepatic and cystic ducts and to related procedures, including those involving cholecystectomy, papillotomy, polypectomy and sphincterotomy, as well as biopsies, placement of stents and the use of cytology brushes.

Figure 1:
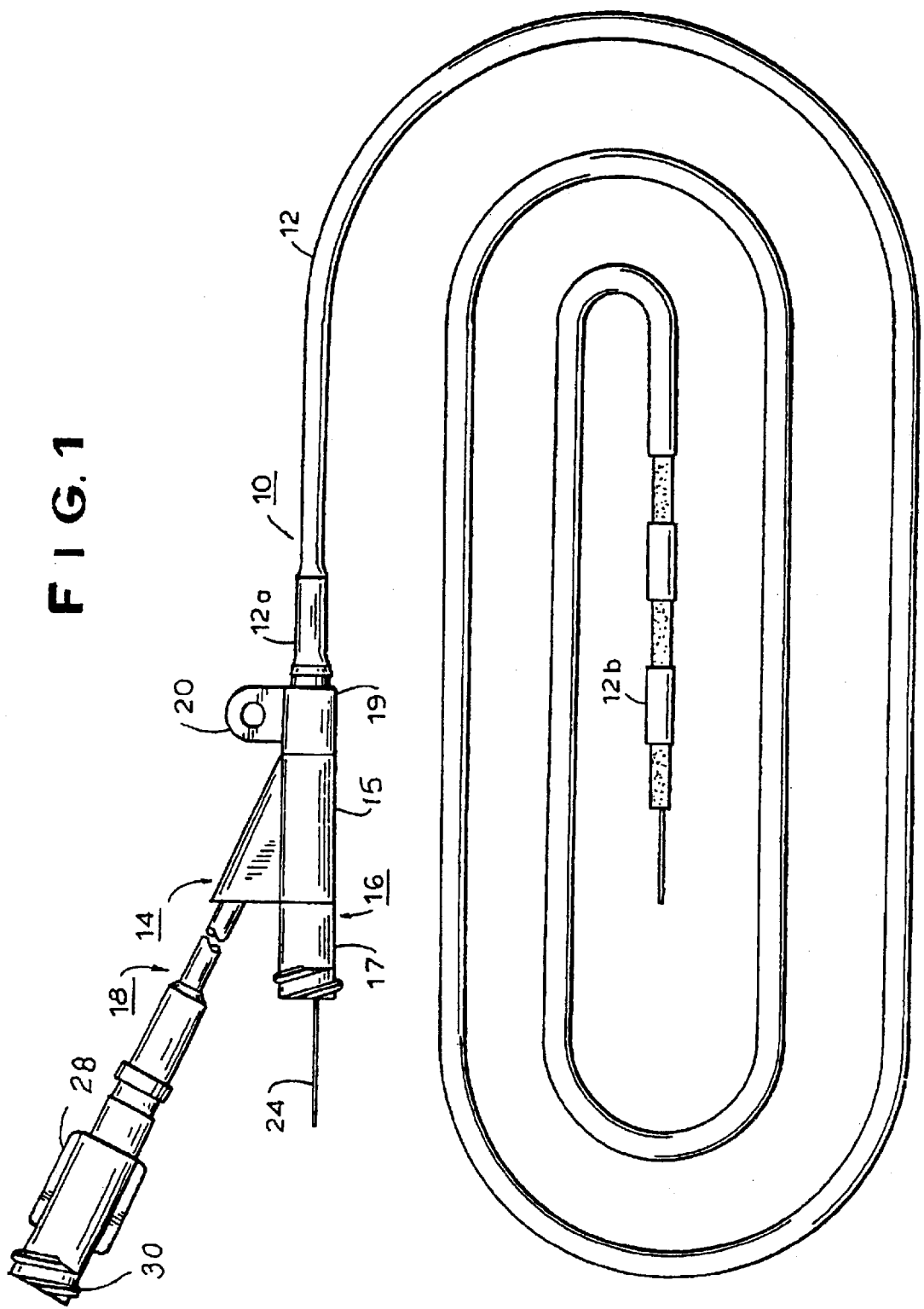
FIG. 1 is an overall view of a dual-lumen biliary catheter of the present invention.
Figure 2:
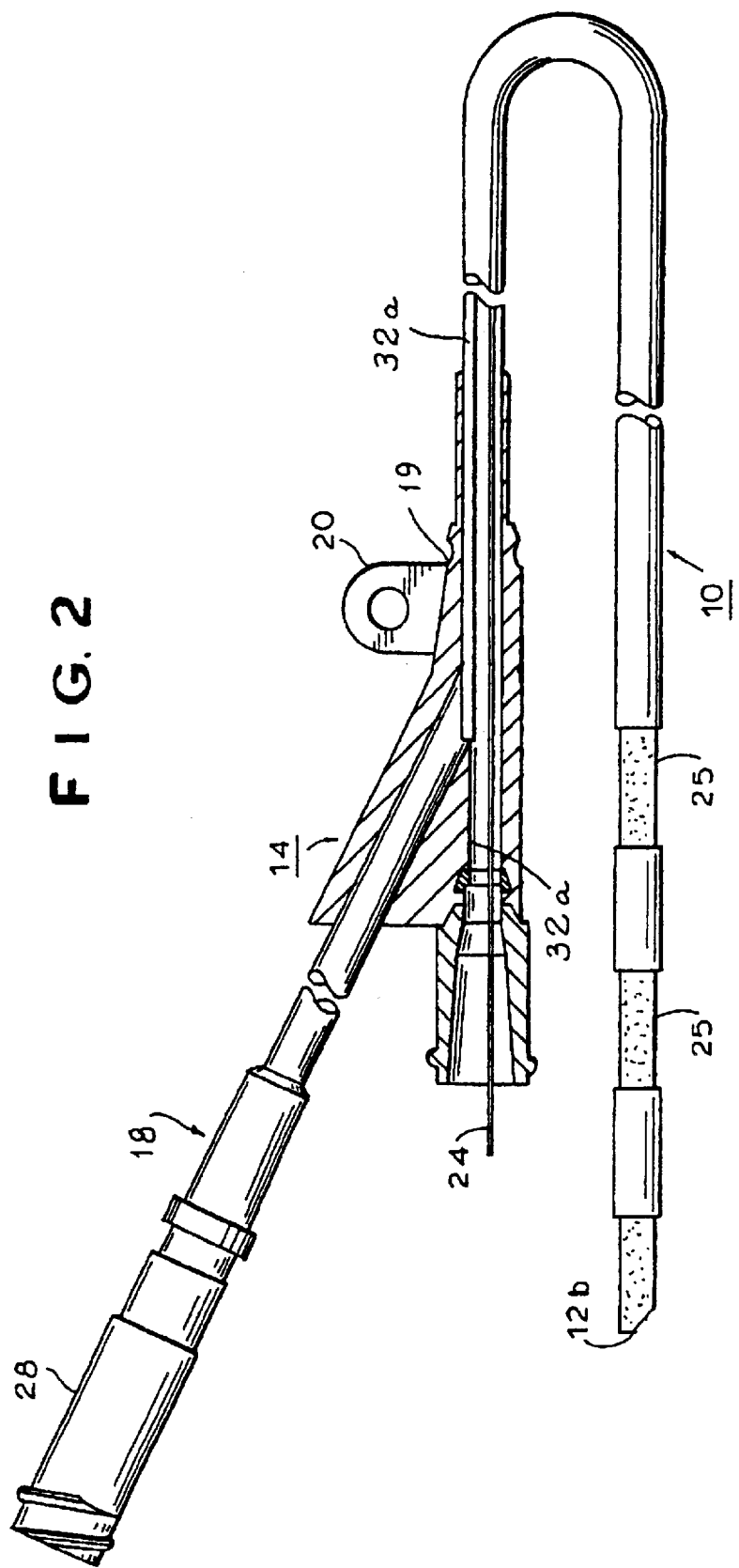
FIG. 2 is a partially broken away, partial section view on an enlarged scale as compared to FIG. 1 of a dual-lumen biliary catheter of the present invention.

Referring generally to FIGS. 1–3, a dual-lumen biliary catheter 10, constructed in accordance with the present invention, is illustrated. In FIG. 1, showing a preferred embodiment of a dual-lumen catheter, the catheter of the present invention comprises a cannula or tubular catheter body 12 having a proximal end 12a for connection to a branching connector 14 and a distal end 12b for insertion into the biliary duct of a patient. Tubular body 12 has a substantially circular cross-sectional shape and a uniform outer diameter. Two independent lumens extend lengthwise thereof and exit through separate ports at the distal tip. Preferably, the catheter is provided with a tip having a relatively sharp bevel, although unbevelled blunt tips and conically formed tips may sometimes be employed. For reasons which will be understood from the following explanation, the two lumen ports within the tip are oriented so that they face forwardly and substantially along the path of advance of the catheter.

Tubular body 12, in a preferred embodiment of a biliary catheter, has a length of approximately 200 cm. This length is sufficient to allow the catheter 10 to be inserted endotracheally into a patient via an endoscope and to reach within the biliary and pancreatic ducts located adjacent the patient's duodenum via an attached fiberscope during an ERCP procedure.

Figure 4:
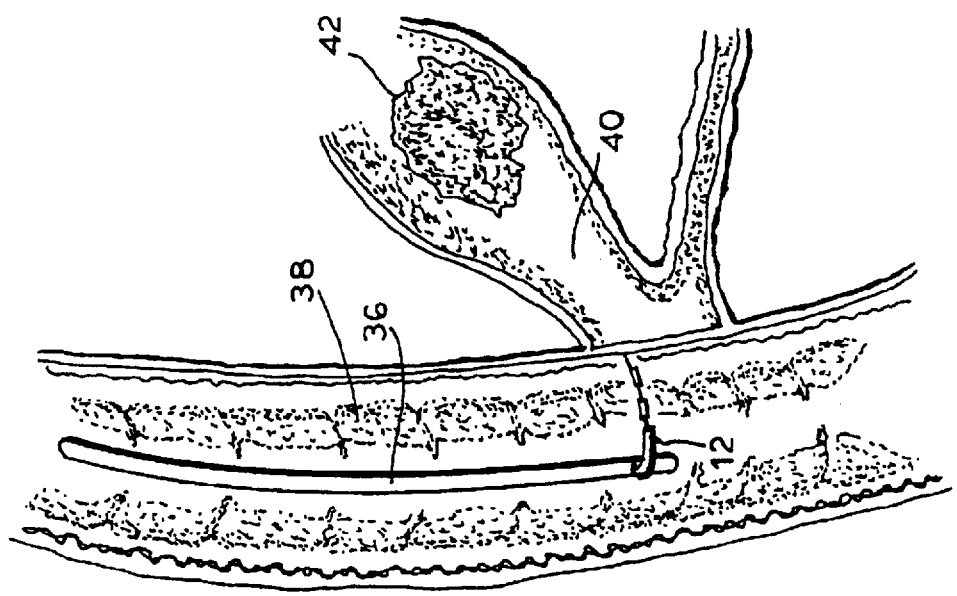
FIG. 4 illustrates a biliary catheter of the present invention through an endoscope accessory channel at the point of introduction into the common biliary duct.

The proximal end 12a of catheter body 12 attaches to branching means 14 which couples the body 12 to spring wire guide feeding means 16 and contrast medium infusion means 18. In a preferred embodiment as shown in FIGS. 1, 2 and 4, branching means 14 comprises a polymeric branching connector 15 which joins the spring wire guide feeding means 16 and contrast medium infusion means 18. The branching connector 15 may include a connector 19 having an affixed apertured wing 20.

Referring to FIGS. 1 and 2, the spring wire guide feeding means 16, in a preferred embodiment, comprises a port having an eighteen gauge luer lock hub 17 which is affixed to the branching connector means 14. The spring wire guide feeding means 16 is utilized to feed a spring wire guide 24 into and out of one lumen of the catheter 10. A spring wire guide utilized in the embodiment of FIGS. 1–3A preferably has a diameter of about 0.035 inches. The use of a spring wire guide having this diameter permits the spring wire guide to be used for placing an indwelling stent, to be discussed below.

Figure 7:
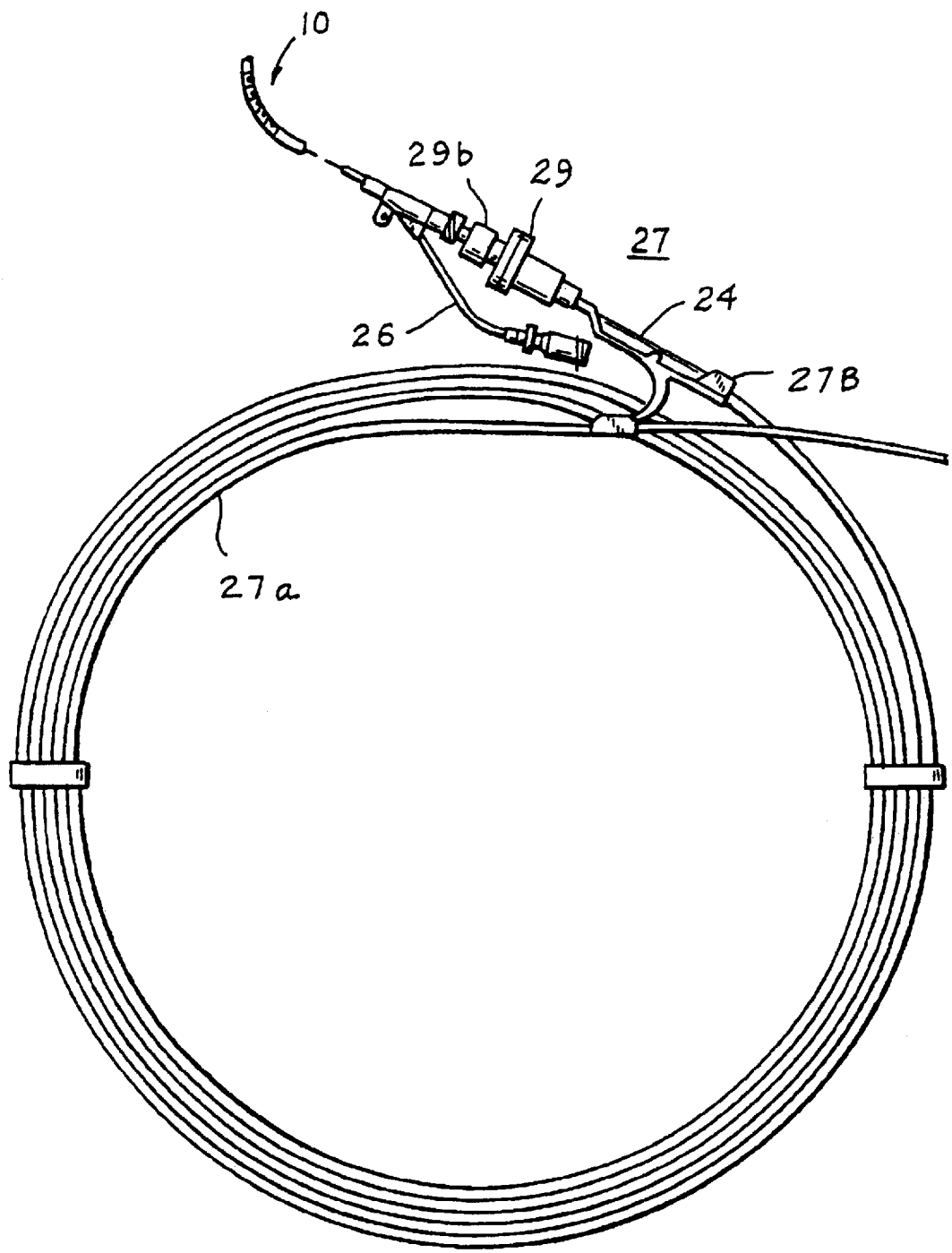
FIG. 7 illustrates the catheter including guide wire feed apparatus utilized with the present invention.
Figure 8:
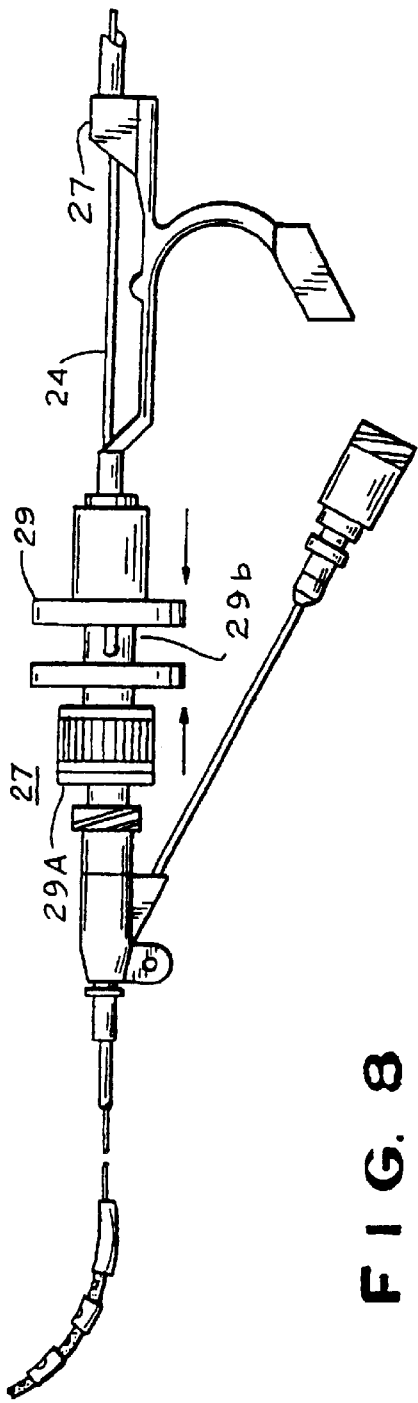
FIGS. 8 and 8A illustrate views illustrating the unlocked and locked position of a guide wire locking mechanism used with the invention.
Figure 8A:
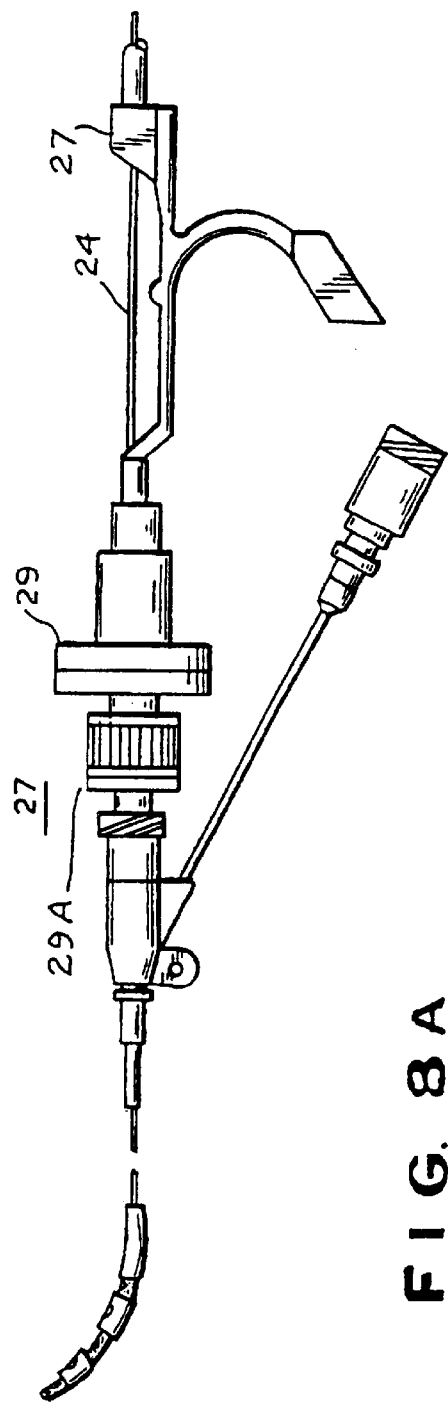
Figure 13A:
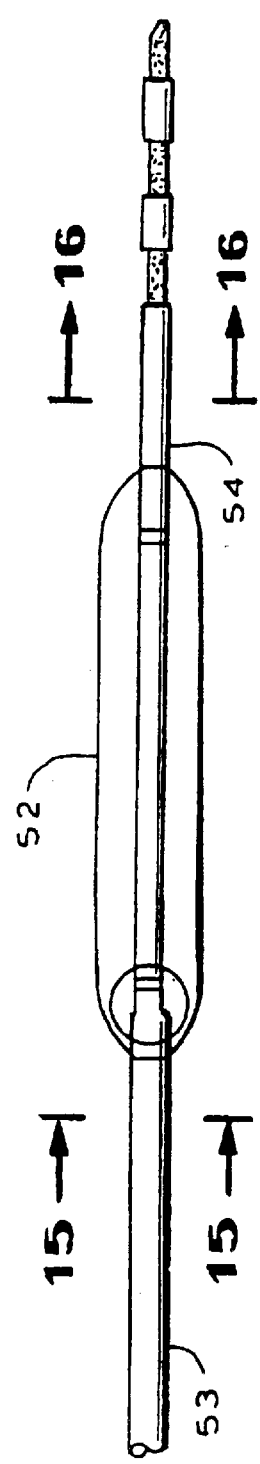
FIGS. 13A and 13B illustrate the distal and proximal end sections, respectively, of a triple-lumen dilatation balloon catheter formed according to the invention.
Figure 13B:
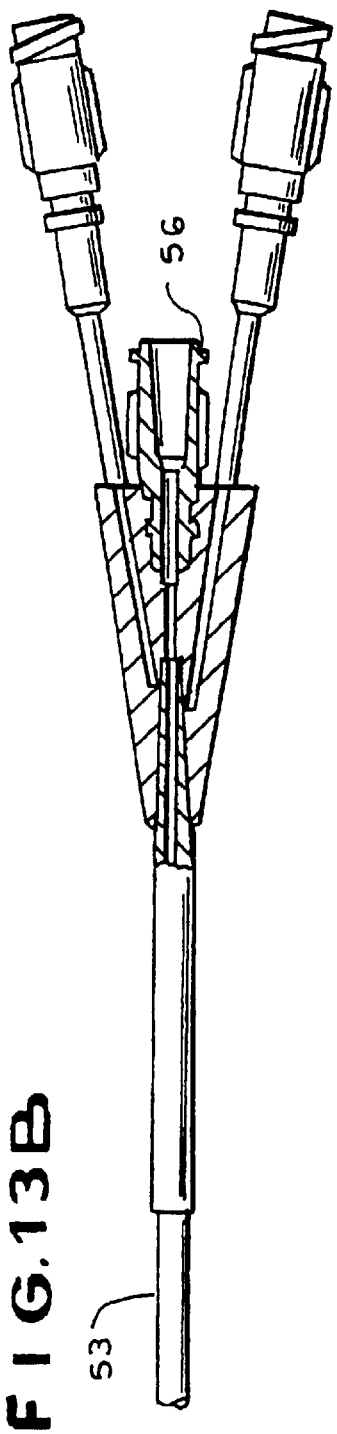
Figure 14:
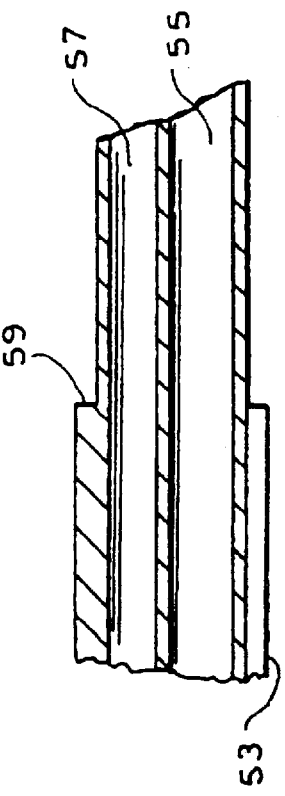
FIG. 14 is a detail view on an enlarged scale, in section, of a portion of the catheter of FIGS. 13A and 13B.

The spring wire guide 24 may optionally be coated with Teflon® in order to add to its lubricity. The spring wire guide of the present invention is preferably fed and withdrawn with the assistance of an auxiliary apparatus, such as the spring wire guide feed apparatus disclosed in U.S. Ser. No. 07/608,234 entitled "Hand Held Device For Feeding A Spring Wire Guide", filed Nov. 2, 1990, and now U.S. Pat. No. 5,125,906 assigned to Arrow International Investment Corp., assignee of the present invention, and which is incorporated herein by reference. An overall view of such a device 27 is illustrated in FIG. 7. Device 27 includes an elongated coiled conduit 27a within which the spring wire guide 24 resides when not in use and a feed device 27b which allows for hand feed of the wire. As shown in FIGS. 7, 8 and 8A, the spring wire guide feed device 27 is preferably affixed to the inlet hub of a wire clamping means, such as snap lock adapter 29 for locking the position of the wire. Snap lock adapter 29 basically comprises a knob 29a which cams a tubular portion 29b radially inwardly to grip the spring wire guide upon relative movement of the parts toward one another. FIGS. 8 and 8A illustrate the respective unlocked and locked positions of the adapter.

Referring to FIGS. 1 and 2, the contrast medium infusion means 18, in a preferred embodiment, preferably comprises a polymeric tube 26 which includes a twenty-gauge connector 28 secured to tube 26 at one end. The connector 28 has a threaded outer surface 30 onto which a cap or stopper (not shown) may be affixed. The interior 28a of the connector 28 is typically luer shaped and is designed to be coupled to a syringe containing radio-opaque contrast medium or dye. The contrast medium or dye is injected down tube 26 and into a contrast medium lumen 34 of the catheter, as discussed below.

Referring to FIGS. 2 and 3, the distal end 12b of the tube 12 is shown in detail. The distal end of the catheter includes a bevelled tip portion 12b and means 25 extending proximally of the tip portion for rendering sections of contrasting the outer distal surface of catheter radio-opaque. Contrast means 25 facilitates the visual identification of the distal end of catheter 10 by the endoscope. In a preferred embodiment, means 25 comprises a plurality of non-toxic ink stripes 25a, formed using an ink such as is sold under the specification 2920 by Gem Gravure of West Hanover, Massachusetts. It is to be appreciated that contrast stripes 25a comprising other materials may be utilized in the catheter of the present invention. Moreover, it is to be appreciated by those skilled in the art that the entire catheter 10, or portions thereof, may be or applied with any acceptable contrast medium. As shown in FIGS. 9A and 9B, the tip 12b of the catheter may be calibrated as at 25a at predetermined intervals, such as 5 mm.

As further illustrated in FIGS. 1–3, 9A and 9B, the preferred catheter tip 12b is beveled to facilitate ease of insertion and passage. A relatively steep bevel has been found to be an optimal configuration in that it is relatively easy and non-traumatic to position the catheter and affords reasonable resistance to bending and buckling.

Referring to FIGS. 3 and 3A, the lumens 32, 34 of a preferred form of dual-lumen catheter 10 of the present invention are shown so as to detail their cross-sectional shape. The catheter 10 includes spring wire guide lumen means 32 and contrast medium lumen means 34. The lumen means 32, 34 extend along the entire length of the catheter body, along parallel paths between the proximal end 12a and distal end 12b. Referring to FIGS. 9A, 9B and 10, distal end 12b is shown bevelled with the contrast medium lumen means 34 terminating just distally of the spring wire guide lumen means 32. In all embodiments, lumens 32 and 34 exit through ports in the distal tip which are oriented so that they face generally lengthwise or axially of the catheter. As illustrated in FIGS. 9A and 10, the contrast lumen port 34 is located in the perpendicular portion of the tip, whereas the major portion of the guide wire lumen port is in the beveled position. In biliary catheters, it is preferred that the port for lumen 32 be within about one-quarter inch of the distal tip. Preferably, the dye lumen is at the tip so as to eliminate interference with dye flow by the side walls of a narrow passageway and/or by the guide wire.

As best shown in FIGS. 3A and 10, spring wire guide lumen means 32 is circular in cross-section and has a diameter of about 0.05 mm to allow passage of a 0.035 mm wire guide, a stent or other device of similar size. The top of spring wire guide lumen 32 is defined by an arcuate septum 32a which defines the interior sidewall of the contrast medium lumen 34. In a preferred dual-lumen embodiment, contrast medium lumen 34 is crescent shaped. While certain preferred embodiments of the present invention are described in the context of a biliary catheter having dual lumens, the present invention, such catheters having more than two lumens. Further, while the present invention is described with respect to a contrast medium lumen 34 having a crescent shape as a means of maximizing lumen size within a relatively small diameter catheter body, certain of the objectives of the invention may be achieved when the contrast medium lumen assumes one of a plurality of other geometric shapes.

Catheters of the present invention may be constructed from extrudible polymers. Preferable proportions are about 18–22 wt. % barium sulfate, about 40 wt. % to about 60 wt % nylon 11 and about 20 wt. % to about 40 wt. % PEBA. A blend of 60 wt. % nylon 11, 20 wt. % PEBA and 20 wt. % barium sulfate is especially preferred. Nylon 11 sold under the trademark BESVOA and PEBA sold under the trademark Pebax are available from Elf Atochem, Philadelphia, Pa. The barium sulphate allows for easy visualization and catheter location under fluoroscopy and has been observed to increase stiffness. This blend is readily extruded into multi-lumen catheters having an o.d. ranging from 3.8 mm down to about 1.8 mm. Catheters formed from this blend have the requisite balance of torqueability, resistance to bunching and stretching and good flexibility.

A further important feature of the present invention is the addition of a hydrophilic coating on the outer surface of the catheter 10 and optionally within the spring wire guide lumen 32. The hydrophilic coating, when applied to the catheter, imparts suppleness and kink resistance to the catheter. The hydrophilic coating further apparently reduces the hardness of the polyurethane or nylon. The hydrophilic coating of the preferred embodiment comprises Methylene Chloride (MeCl), Polyethylene Oxide (PEO) and Tyrite 7617 Adhesive.

The hydrophilic coating is preferably applied to the catheter pursuant to the following process. Initially, 1400 ml of Mecl is poured into a container which is placed on stirrer plate. A stirring magnet is then dropped into the beaker, and the stirring plate is activated. Stirring is adjusted until a vortex forms. Next, 14.91 g.±0.02 g. of PEO are slowly added to the stirring solution. The solution is stirred continuously for about 10 minutes in order to break up any lumps of PEO. Using a syringe, about 15.75 ml Tyrite 7617 adhesive is added to the stirring solution which is stirred for an additional five minutes. The stirred solution is then poured into a treatment tank.

The catheter 10, with its end sealed off, is then dipped into the tank until the portion to be coated is immersed. The catheter 10 is left in the tank for about 1 second, quickly retrieved and the excess solution allowed to drip into the tank. The catheter is then air dried for about 8 hours.

The catheter 10 with hydrophilic coating provides a highly lubricated surface which is activated by the biliary fluids of the patient. The hydrophilic coating may also be activated by the gastric fluids which enter the endoscope. The hydrophilic coating reduces the durometer of the catheter and imparts kink resistance and suppleness to the catheter. The coating has been found to yield a lower coefficient of friction than that of comparable Teflon® catheters. While the present invention is being described in the context of a preferred hydrophilic coating, it is to be appreciated that other hydrophilic coatings may be utilized in the present invention. Examples of such hydrophilic coatings are found and described in U.S. Pat. No. 4,943,460 entitled "Process for Coating Polymer Surfaces and Coated Products Produced Using Such Process." Another hydrophilic coating is Hydromer® "Slippery When Wet" coating manufactured by Hydromer, Inc. of Whitehouse, N.J. Preferably, the slippery coating is not applied to the proximal end section of the catheter so as to facilitate manual manipulation thereof during catheter placement.

Figure 5:
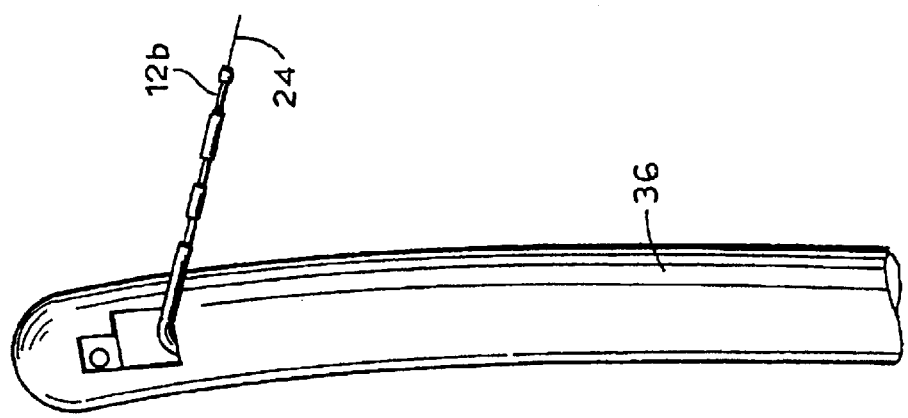
FIG. 5 is an enlarged detailed view of a catheter of the present invention illustrating its exit from the distal tip of the accessory channel of the endoscope.

The operation and use of the biliary catheter 10 as so far described is now explained with reference to FIGS. 1 through 5. Initially, the patient is sedated or, in rare situations, placed under general anesthesia. Using the spring wire guide advancer, the wire guide 24 is inserted through an endoscope and exits through the side of an attached fiberscope 36, the end of which is shown in FIG. 5 is situated in the patient's duodenum 38. The catheter 10 is then threaded over the spring wire guide 24 via spring wire guide lumen 32 and fed through the accessory channel 36 and both catheter and wire guide are advanced into the common bile duct 40.

Next, a pre-filled syringe of radio-opaque dye or contrast medium is attached to a connector 28. A sufficient amount of dye to fill the catheter is then injected into tube 26. A clamp or adhesive tape may be used to lock the relative positions of the catheter and spring wire guide. An example of a clamp which achieves the function is a clamp of the Series 340 clamps marketed by Halkey Medical of St. Petersburg, Fla. Contrast medium is then injected into the contrast medium lumen 34 which exits at distal end 12b and into the common biliary duct 40, thereby permitting X-ray or fluoroscopic visualization of the duct 40. Digitized markings 25a facilitate precise adjustment of the catheter. If the position of the catheter needs to be adjusted, the spring wire guide 24 is advanced and the catheter 10 advanced accordingly. The catheter can be rapidly adjusted and contrast medium or dye can be repeatedly infused without the need for repeated insertion and removal of the spring wire guide 24.

The present invention-thus provides for probing with the spring wire guide 24 via lumen 32 and the injection of contrast medium or dye via contrast medium lumen 34, further probing and further injection of dye until a proper catheter position is achieved. The present invention eliminates the time consuming step of removing the spring wire guide 24 prior to each change in catheter position and contrast medium infusion. The use of the catheter of the present invention can save over 20 minutes of time during a typical ERCP procedure. In addition, a laser fiber for biliary lithotripsy can be placed through one lumen with ongoing injection of contrast medium or fluid in the second lumen. Further, selective cannulation of the right and left hepatic ducts, cystic ducts or pancreas becomes more directed, safe and efficient.

A particular feature of the present invention is its adaptability for use in placing a stent around a biliary calculus 42 or cystic or pancreatic obstruction. In approximately 5% of all ERCP cannulations, surgery is mandated. However, surgery is often not always possible at the time of the ERCP procedure. In such situations, a stent is typically placed within the common biliary or pancreatic duct around the calculus.

As used in one procedure for stent placement, the catheter 10 is utilized in association with a spring wire guide 24 having a length greater than twice the length of the catheter 10, or over 400 cm in length. The spring wire guide may be threaded with the catheter into the endoscope, as described above. The spring wire guide utilized in this embodiment should preferably have a diameter of about 0.035 inches. The stent is tubular with a longitudinally extending slit which permits it to be fitted over the wire guide.

The spring wire guide is advanced to a desired position within the common biliary duct and the catheter then advanced relative to the wire into a final position. Contrast medium or dye is infused, and the calculus 42 is located, as shown in FIG. 6. The catheter 10 is then removed from the endoscope.

Because the spring wire 24 guide has a length greater than twice that of the catheter 10, the catheter 10 can be completely removed from the endoscope over the spring wire guide 24 without the need for withdrawing the spring wire guide. After the catheter 10 is removed, a stent may be placed forward of the catheter over the spring wire guide. The catheter is utilized to push the stent into the endoscope, over the spring wire guide, into the common biliary duct and around the biliary calculus 42. When the stent is in position, the spring wire guide 24 is then removed along with the catheter.

A catheter, as shown in FIGS. 3 and 3A, having a balloon adjacent its distal tip, as shown in FIG. 3B, may be used with a wire having an iridium charge placed in its distal tip so as to dispose iridium for treatment in the biliary tract. In this treatment application, the wire employed is preferably a 0.035 inch wire and is passed through a nasal passage using an endoscope. After the wire is positioned within the biliary tract, the endoscope is removed and the catheter is advanced over the guide wire using lumen 32 as the guide wire lumen adapted to be passed through round lumen 32 having a diameter of 0.040 inches. Lumen 34 serves as the inflation lumen and exits in a radial port for inflation of the balloon. The overall diameter of the catheter is 2.8 mm. Once the iridium, which may be fitted into the tip of the catheter at 35, is properly placed, the balloon is inflated through lumen 34 to maintain both catheter and iridium in place. Although the catheter may be deployed orally as in other procedures due to the length of the iridium treatment, the catheter is preferably inserted through a nasal passage.

Catheters having the cross-section of FIG. 3 are also useful for tissue sampling with a brush. In this application, lumen 32 preferably has a diameter of about 0.040 inches.

Lumen 34 is utilized for a saline solution for the purpose of cleansing the tissue to be sampled prior to obtaining the sample with the brush.

A triple-lumen catheter used in the practice of polypectomy is disclosed in FIGS. 11 and 12. The catheter illustrated in FIGS. 11 and 12 has a first lumen 48 dimensioned to pass a polypectomy snare, a second lumen 49 through which an injection medium will be passed and a retrieval lumen 50 for passage of a basket or other retrieval device. Lumen 49 or lumen 50 may be used to pass a flexible plastic or stainless steel needle for injecting a polyp once it is visualized to further assist the physician in excising the polyp with a snare. As indicated in FIG. 11, where a snare is illustrated projecting from the lumen port 48, the snare is a device which uses radio frequency energy to cauterize the root of the polyp and the energy so used exists through a plate in which the patient is seated. Once the polyp is incised, a net, basket or other retrieval device of known construction is passed through lumen 49 for grasping and retrieval of the polyp through the lumen. If a large polyp is to be removed, the catheter itself is removed at this point. The catheter of FIGS. 11 and 12 has an external diameter of 2.5 mm. The snare lumen has a diameter of 0.5 mm, whereas the lumens 49 and 50 have diameters of 0.4 mm. Lumen 48 exits through the bevelled portion of the distal tip, whereas lumens 49 and 50 exit through the portion disposed perpendicular to the long axis of the catheter.

For certain purposes, the dual-lumen catheter configuration of FIG. 12A may be satisfactory for the practice of polypectomy. As utilized, the catheter configuration of FIG. 12A is provided with a lumen 48a of about 0.050 inches in diameter for passage of the snare and a lumen 49a of about 0.040 inches in diameter for the injection needle device. Retrieval is effected by withdrawal of the catheter with the embodiment of FIG. 12A. The catheter illustrated in FIG. 12A preferably has an outside diameter of about 2.8 mm.

Still another embodiment of the invention, as illustrated in FIGS. 13A–16, is a triple-lumen catheter having a dilatation balloon 52 which may be used, for example, to facilitate removal of gall stones by the dilation of a restricted portion of the biliary tract. The catheter of FIGS. 13A–16 has a main body portion 53 of a first uniform outer diameter and a distal tip portion 54 of a smaller uniform outer diameter. Preferably, the distal tip has a bevelled configuration similar to the tip of the embodiment of FIGS. 1–3.

The catheter of FIGS. 13A–16 has a first lumen 55 which extends lengthwise thereof from a connector 56 to an exit port at the distal tip in the manner illustrated in FIG. 10. Lumen 55 is preferably sized to permit the passage of a 0.035 inch guide wire. A second crescent shaped lumen 57, as illustrated in FIGS. 15 and 16, also exits in a port at the distal tip and provides for the injection of tracer dye. The catheter is also provided with a third lumen 58 which exits in a shoulder 59 separating the larger diameter main body portion 53 from the smaller diameter tip portion 54. Lumen 58 is provided for the delivery of an inflation medium for inflating the balloon 52. The inflation medium employed is desirably an incompressible fluid and is typically a saline solution. The fluid may include a tracer dye to permit visualization of the balloon by fluoroscopy. The catheter of FIGS. 13A–16 has a maximum diameter of 2.8 mm to allow for passage through the accessory channel of an endoscope and a diameter of approximately 1.8 mm in the distal tip portion. The use of a smaller diameter distal tip portion facilitates passage into more remote portions of the biliary tract and also provides room for packing the uninflated balloon so that it does not project appreciably beyond the surface of the large diameter catheter body portion.

In use, the catheter of FIGS. 13A–16 is advanced utilizing the wire guide, as described above, until the desired position is reached, utilizing a tracer dye and fluoroscopy to assist in the guidance of the catheter to the desired location. Balloon 52 is inflated when the event a stricture in the biliary duct is encountered. Once the duct is dilated, stones encountered may, in many cases, dislodge and begin to remove themselves naturally, but if need be, a stent may be inserted to maintain patency of the duct to encourage the passage of the stone or the guide wire may be removed and an extractor device may be employed utilizing lumen 55.

Figure 17A:
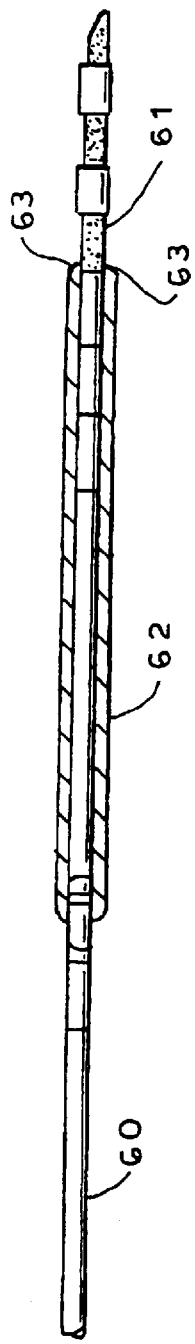
FIGS. 17A and 17B illustrate the distal and proximal end sections of a multi-lumen catheter in placing a stent.
Figure 17B:
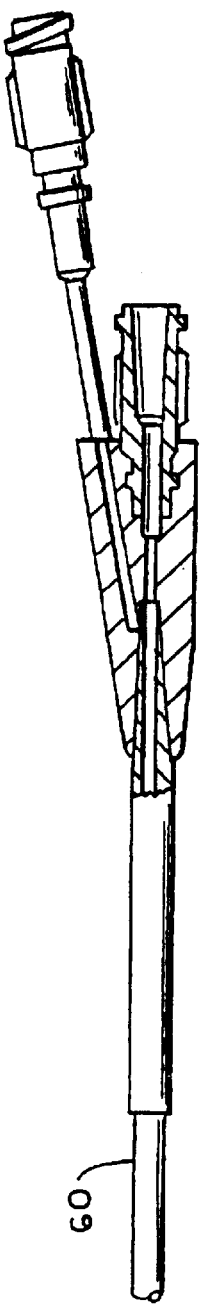
Figure 18:
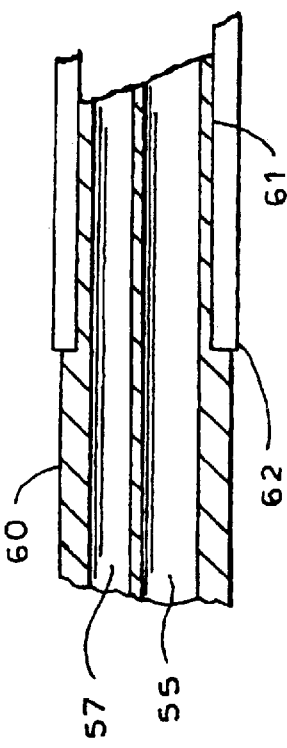
FIG. 18 is a sectional view enlarged with respect to FIGS. 17A and 17B illustrating the distal portion of the catheter with the stent in position.

FIGS. 17A–18 illustrate a catheter having utility for the placement of a stent in the biliary tract. The catheter of FIGS. 17A–18 is similar in structure to the catheter of FIGS. 13A–16 in that it has a main body portion 60 of a first diameter and a distal tip portion 61 of a second similar diameter on which a stent 62 is supported. In the illustrative embodiment, the distal portion 61 has an outer diameter of 1.8 mm which is suitable for supporting a 10 French tubular stent formed of a biologically inert material, such as polyurethane. As seen in FIG. 18, when stent 62 is placed on the distal tip portion, its proximal end surface bears against a shoulder formed between the larger diameter body portion 60 and the reduced diameter distal end portion 61. In the illustrative embodiment, main body portion 60 has an outer diameter of 2.8 mm for passage through a 3.2 mm endoscope accessory channel. The outer diameter of stent 62 is approximately 3 mm. The catheter of FIGS. 17A–18 is provided with two independent and continuous lumens 55 and 57 preferably having the configurations of the lumens in FIG. 16. Lumen 55 is dimensioned to accept a 0.035 wire guide which exits at the distal tip. The crescent shaped lumen 57 provides for the injection of tracer dye for use in visualization of the passage and location of the stricture where the stent is intended to be placed. In use, the catheter is advanced over the wire guide using the tracer dye to assist in placing it. When the stricture is located and the stent properly positioned, the catheter and guide wire are withdrawn leaving the stent in place. As is known in the art, stent 62 is provided with barbs 63 which hold the stent in position as the catheter is withdrawn. The barbs are yieldable upon application of a predetermined force by a retrieval device when it is desired to remove the stent. An advantage of the embodiment of FIGS. 17A–18 is that the relatively small diameter distal portion relatively easily negotiates restricted portions of the duct. The procedure is facilitated by the existence of the guide wire within the catheter which provides a certain degree of stiffness to the catheter and resistance to kinking.

Catheters having three or more lumens, as illustrated in FIGS. 11–16, allow for the performance of other procedures in conjunction with ERCP or the use of a lighting device while allowing the spring wire guide to remain in place. Triple-lumen catheters having outside diameters ranging from 3.8 mm down to about 1.8 mm may be extruded utilizing the resin blends described above with three lumens having inside diameters of 0.5 mm with a minimal wall thickness of 0.005 inches. One such lumen will accommodate an 0.018 mm spring wire guide, while the second lumen is reserved for infusion of contrast medium, and a third such lumen is reserved for additional instruments, such as a papillotome or sphincterotome, a snare, a basket and other accessories, such as forceps, stone extractor, biopsy cutters- or direct visualization lighting devices. Additionally, a lumen may be provided which exits radially at a location spaced adjacent the distal tip for inflation of a dilation balloon used for dilating the tract for removing bile stones or a previously introduced stent. Catheters formed in accordance with the invention are useful for the endoscopic examination and treatment of other parts of the gastrointestinal system as well. Multi-lumen catheters can be provided with outer diameters of 3.8, 2.8 and 1.8 mm which allow for use with standard endoscopes having channels with internal diameters of 4.2, 3.2 and 2.2 mm, respectively.

An important advantage of a catheter having three or more lumens is that the guide wire may be maintained within its lumen while performing a procedure involving advancement of a device, such as a cytology brush, papillotome or an optical visualizer, allowing a third lumen to be reserved for the injection of dye. The presence of the guide wire serves to prevent kinking and collapse of all lumens, thus allowing for unimpeded advancement of the device employed, dye injection and/or aspiration of bile for laboratory analysis through a lumen not contaminated with dye. The guide wire also facilitates switching from one device to another. When using an optical device, a fourth lumen may be advantageously reserved for injection of saline solution to clear the area being visualized prior to use of the device.

Further specific embodiments and procedures of use for multi-lumen catheters formed according to the invention are described with particular reference to the cross-sectional views of FIGS. 19–24.

FIG. 19 is a cross-section of a multi-lumen catheter utilized for disposing two 0.035 inch guide wires simultaneously, one within the pancreatic duct and one through the cystic duct through lumens 70 and 71, utilizing contrast medium injected through lumens 72 and 73. Once the guide wires are in place, the catheter of FIG. 19 is withdrawn and individual catheters advanced over the selected guide wire for catheterization of either the pancreatic or cystic duct. The catheter of FIG. 19 preferably has an outer diameter of about 2.8 mm. The catheter of FIG. 19 is of advantage when an uncertainty exists as to the extent and location of patient stress.

FIG. 20 illustrates a cross-section of a catheter with which a papillotome is used for tissue cutting as an aid for catheter insertion. In use of the catheter of FIG. 20, circular lumen 74 is reserved for a papillotome which is preferably permanently mounted the lumen. Placement of the catheter of FIG. 20 involves use of additional lumen 75 for a guide wire and additional lumen 76 for contrast medium in the manner described above with respect to FIGS. 1–12. The catheter of FIG. 20 preferably has an outside diameter of about 2.8 mm.

FIG. 21 is a cross-section of a catheter useful in procedures for stone removal. Lumen 78 (upper) is used for the passage alternatively of a guide wire or a fiber optic device for visualization of stones. Lumen 79 is reserved for passage of a stone basket. Alternatively, the catheter of FIG. 21 may be equipped with a dilatation balloon adjacent its distal tip which is inflated with an incompressible medium. After placement of the distal tip, the balloon is inflated to dilate the duct to effect dislodgment of the stone. A catheter so constructed will have an outside diameter of approximately 2.8 mm. At the option of the physician, the guide wire may be removed and replaced with the optical device for visualization of the stone removed by the basket or by dislodgment with the balloon.

An alternative use of a catheter having the configuration of FIG. 21 includes use of a vacuum assist for stone removal by application of a vacuum to one of the lumens while reserving the other either for a stone retrieval basket or as the inflation lumen for the balloon. To maximize lumen size in this application, the catheter preferably has an outside diameter of about 3.8 mm.

The cross-sectional view of FIG. 22 depicts an alternative form of catheter used for visualization and removal of gall stones. As illustrated in FIG. 22, lumens 82, 83 are used for injection of contrast medium and for a guide wire respectively. Lumen 84 is reserved for a basket for the removal of stones. Once the catheter is within the biliary tract, the guide wire is removed from lumen 83 and replaced with a fiber optic visualization device to confirm that the stone, not a air bubble, is present. The basket is then manipulated through lumen 84 to retrieve the stone. The catheter of FIG. 22 has an outside diameter of about 2.8 mm.

FIG. 23 is an end view of triple-lumen catheter alternative to that shown-in FIG. 15 in which the inflation lumen, shown at 86, is an annular lumen. As in FIG. 15, the catheter in a preferred form is provided with a circular lumen 87 for a 0.035 inch guide wire and a crescent-shaped lumen 88 for injection of contrast medium. The catheter of FIG. 23 preferably has a 2.8 mm outside diameter and is in other respects substantially the same as the embodiment illustrated in FIGS. 13A–16.

FIG. 24 illustrates an end view of a modified version of the catheter of FIGS. 17 and 18. According to FIG. 24, the catheter depicted has a guide wire lumen 90, a retrieval lumen 92 for a basket or snare and a dye lumen 94, all extending through the reduced diameter distal tip portion. Except for the inflation lumens, the lumens in FIGS. 19–24 extend continuously and independently and exit through axially facing ports. The catheter of FIG. 24 has a maximum outside diameter of about 3.8 mm. The reduced diameter distal portion has a diameter of about 2.8 mm which allows for support of a 7 French stent 95 having its circumference flush with the circumference of the remainder of the catheter. Once the stent is visualized, the snare is utilized to grasp its proximal end. The stent is withdrawn by withdrawing the snare and, if necessary, the catheter until the stent is within the large intestine where it may be released. Thereafter, the guide wire is used to locate the tip of the catheter at the desired location with the biliary or cystic duct. The catheter is withdrawn with the stent remaining in place and the catheter then removed further until it is within the intestine. The snare or basket is then used to pick up the old stent and the endoscope and catheter are-then withdrawn from the body.

The present invention has been described with reference to the attached Figures and described embodiments. It is to be appreciated that other embodiments may fulfill the spirit and scope of the present invention and that the true nature and scope of the present invention is to be determined with reference to the claims appended hereto.

What is claimed:

1. A method of dilating a duct of a patient using a catheter having at least three lumens, two of said lumens having a distal opening at a distal tip of said catheter, and a third lumen communicating with a balloon disposed proximal to said distal tip of said catheter, a first lumen of said catheter having a wire threaded therethrough, comprising the steps of:

threading said catheter and said wire guide through an endoscope and into said duct to a desired position;

infusing a contrast medium through a second lumen of said catheter to release contrast fluid from the distal tip of the catheter and visualize said duct through the use of said contrast medium while maintaining said wire guide in said first lumen of said catheter; and inflating said balloon to dilate said duct by infusing a fluid through a third lumen of said catheter.

2. The method of claim 1, wherein the method comprises, more specifically, selecting a catheter wherein the first and second lumens end in independent axially facing ports in the distal end of the catheter.

3. A method of dilating a duct of a patient using a catheter having at least three lumens, a first of said lumens having a distally facing distal opening at a distal tip of said catheter, a second of said lumens having a generally distal facing distal opening adjacent the distal tip of the catheter and a third lumen communicating with a balloon disposed proximal to said distal end of said catheter, a first lumen of said catheter having a wire threaded therethrough, comprising the steps of:

threading said catheter and said wire guide through an endoscope and into said duct to a desired position;

infusing a contrast medium through a second lumen of said catheter to release contrast fluid from the catheter and visualize said duct distally of the balloon through the use of said contrast medium while maintaining said wire guide in said first lumen of said catheter; and inflating said balloon to dilate said duct by infusing a fluid through a third lumen of said catheter while maintaining said wire guide in said first lumen of said catheter.

4. The method according to claim 3, wherein the method further comprises releasing contrast fluid into the duct through the second lumen while the balloon is inflated.

5. A method of dilating a duct of a patient using a catheter having at least three lumens, two of said lumens having a distal opening at a distal tip of said catheter, and a third lumen communicating with a balloon disposed proximal to said distal tip of said catheter, a first lumen of said catheter having a wire guide threaded therethrough, comprising the steps of:

threading said catheter and said wire guide through an endoscope and into said duct to a desired position;

infusing a contrast medium through a second lumen of said catheter to visualize said duct through the use of said contrast medium while maintaining said wire guide substantially within said first lumen of said catheter such that said duct may be visualized through the use of said contrast medium without requiring the removal of said wire guide from said duct or said first lumen; and inflating said balloon to dilate said duct by infusing a fluid through a third lumen of said catheter.

6. The method according to claim 5, wherein the method further comprises releasing contrast fluid into the duct through the second lumen while the balloon is inflated.

7. A method of visualizing a duct of the biliary tree, the method comprising:

(a) selecting a catheter having a first lumen configured for receiving a wire guide, a second lumen configured for injecting contrast fluid, the first and second lumens terminating at the distal end of the catheter, and a third lumen configured for receiving a cutting instrument;

(b) threading said catheter and a wire guide through an endoscope and into said duct to a desired position; and (c) infusing a contrast medium through a second lumen of said catheter to release contrast fluid from the catheter and visualize said duct distally of the catheter.

8. The method according to claim 7, further comprising actuating a cutting instrument in the third lumen to cut tissue.

9. The method according to claim 8, wherein the method comprises, more specifically, using a papillotome/sphincterotome in the third lumen to cut tissue.

10. The method according to claim 7, wherein the method comprises, more specifically, selecting a catheter having a papillotome permanently disposed in the third lumen.

11. A method of visualizing a duct of the biliary tree, the method comprising:

(a) selecting a catheter having a first lumen configured for receiving a wire guide, a second lumen configured for injecting contrast fluid, the first and second lumens terminating at the distal tip of the catheter, and a third lumen configured for receiving a cutting instrument;

(b) threading said catheter and a wire guide through an endoscope and into said duct to a desired position; and (c) infusing a contrast medium through a second lumen of said catheter to release contrast fluid from the distal tip of the catheter and visualize said duct distally of the catheter.

12. The method according to claim 11, further comprising actuating a cutting instrument in the third lumen to cut tissue.

13. The method according to claim 12, wherein the method comprises, more specifically, using a papillotome in the third lumen to cut tissue.

14. The method according, to claim 11, wherein the method comprises, more specifically, selecting a catheter having a papillotome permanently disposed in the third lumen.

15. A method of visualizing a duct of the biliary tree, the method comprising:

(a) selecting a catheter having a first lumen configured for receiving a wire guide, a second lumen configured for injecting contrast fluid, the first and second lumens each terminating in an independent axially facing port in the distal end of the catheter, and a third lumen configured for receiving a cutting instrument;

(b) threading said catheter and a wire guide through an endoscope and into said duct to a desired position; and (c) infusing a contrast medium through a second lumen of said catheter to release contrast fluid from the distal tip of the catheter and visualize said duct distally of the catheter.

16. The method according to claim 15, further comprising actuating a cutting instrument in the third lumen to cut tissue.

17. The method according to claim 15, wherein the method comprises, more specifically, selecting a catheter having a papillotome disposed in the third lumen and using the papillotome to cut tissue.

* * * * *